United States Patent
Jung et al.

(10) Patent No.: US 10,281,520 B2
(45) Date of Patent: May 7, 2019

(54) DIAGNOSING AN ABNORMAL STATE OF A SUBSTRATE-PROCESSING APPARATUS

(71) Applicant: Samsung Electronics Co., Ltd., Suwon-si (KR)

(72) Inventors: Dae-Sung Jung, Pohang-si (KR); Sang-Yoon Soh, Yongin-si (KR); Jung-Hwan Um, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 254 days.

(21) Appl. No.: 15/399,060

(22) Filed: Jan. 5, 2017

(65) Prior Publication Data
US 2018/0059168 A1    Mar. 1, 2018

(30) Foreign Application Priority Data
Aug. 30, 2016    (KR) .......................... 10-2016-0110494

(51) Int. Cl.
| | | |
|---|---|---|
| *G01R 31/00* | (2006.01) | |
| *G01R 31/28* | (2006.01) | |
| *G01N 25/72* | (2006.01) | |
| *H01J 37/32* | (2006.01) | |
| *H01L 21/67* | (2006.01) | |
| *H01L 21/687* | (2006.01) | |

(52) U.S. Cl.
CPC .......... *G01R 31/282* (2013.01); *G01N 25/72* (2013.01); *H01J 37/32724* (2013.01); *H01J 37/32935* (2013.01); *H01L 21/67248* (2013.01); *H01L 21/67259* (2013.01); *H01L 21/67288* (2013.01); *H01L 21/68742* (2013.01); *H01J 2237/332* (2013.01); *H01J 2237/334* (2013.01)

(58) Field of Classification Search
USPC ..... 324/750.03, 750.04, 750.06, 762.05, 511
See application file for complete search history.

(56) References Cited

U.S. PATENT DOCUMENTS

| | | |
|---|---|---|
| 6,469,283 B1 | 10/2002 | Burkhart et al. |
| 8,581,598 B2 | 11/2013 | Fujisawa |
| 2003/0033116 A1* | 2/2003 | Brcka ................ H01L 21/6831 702/182 |
| 2011/0140712 A1 | 6/2011 | Inoue |
| 2015/0043123 A1 | 2/2015 | Cox |

FOREIGN PATENT DOCUMENTS

| | | |
|---|---|---|
| JP | 2008047564 | 2/2008 |
| JP | 4121361 | 7/2008 |
| JP | 5401343 | 1/2014 |
| KR | 1020060100028 | 9/2006 |
| KR | 10585082 | 1/2016 |

* cited by examiner

*Primary Examiner* — Vincent Q Nguyen
(74) *Attorney, Agent, or Firm* — Onello & Mello, LLP

(57) ABSTRACT

A method of diagnosing an abnormal state of a substrate-processing apparatus includes measuring a temperature of a chuck in the substrate-processing apparatus. The temperature of the chuck is compared to a target temperature of the chuck, with a temperature-controlling unit. A control signal is analyzed to diagnose an abnormal state of the substrate-processing apparatus. The control signal is transmitted from the temperature-controlling unit to a drive parameter-applying unit configured to provide the chuck with a drive parameter.

8 Claims, 8 Drawing Sheets

US 10,281,520 B2

DIAGNOSING AN ABNORMAL STATE OF A SUBSTRATE-PROCESSING APPARATUS

CROSS-REFERENCE TO RELATED APPLICATION

This application claims priority under 35 USC § 119 to Korean Patent Application No. 2016-0110494, filed on Aug. 30, 2016, the disclosure of which is herein incorporated by reference in its entirety.

BACKGROUND

A substrate-processing apparatus may be used for processing a layer on a semiconductor substrate. The substrate-processing apparatus may include a chuck on which the semiconductor substrate may be placed. A heater for heating the semiconductor substrate may be arranged in the chuck.

According to related arts, an abnormal state in the substrate-processing apparatus may not be accurately recognized. In particular, inaccurate placement of the semiconductor substrate on the chuck may not be recognized.

SUMMARY

In one aspect, the present inventive concepts are directed to a method of diagnosing an abnormal state of a substrate-processing apparatus comprising measuring a temperature of a chuck in the substrate-processing apparatus. The measured temperature of the chuck is compared to a target temperature of the chuck with a temperature-controlling unit. A control signal is analyzed to diagnose an abnormal state of the substrate-processing apparatus. The control signal is transmitted from the temperature-controlling unit to a drive parameter-applying unit configured to provide the chuck with a drive parameter.

In another aspect, the present inventive concepts are directed to an apparatus for diagnosing an abnormal state of a substrate-processing apparatus comprising a temperature sensor configured to measure a temperature of a chuck in the substrate-processing apparatus. A temperature-controlling unit is configured to generate a comparison result by comparing the measured temperature of the chuck to a target temperature of the chuck, and to transmit a control signal to a drive parameter-applying unit configured to provide the chuck with a drive parameter based on the comparison result. A first analyzing unit is configured to analyze the control signal to diagnose the abnormal state of the substrate-processing apparatus.

In another aspect, the present inventive concepts are directed to an apparatus for diagnosing an abnormal state of a substrate-processing apparatus comprising a substrate-processing apparatus including a chuck configured to hold a substrate. A temperature sense is configured to measure a temperature of the chuck. A temperature controlling unit is configured to generate a control signal in response to a difference between the temperature of the chuck and a target temperature. A drive unit is configured to modify a drive parameter and transmit the drive parameter to the substrate-processing apparatus in response to receiving the control signal. A first analyzing unit is configured to analyze the control signal to determine a type of the abnormal state of the substrate-processing apparatus. A second analyzing unit is configured to analyze the drive parameter to determine the type of the abnormal state of the substrate-processing apparatus.

BRIEF DESCRIPTION OF THE DRAWINGS

These and/or other aspects and advantages of the present general inventive concepts will become apparent and more readily appreciated from the following description of the embodiments, taken in conjunction with the accompanying drawings of which.

DETAILED DESCRIPTION OF THE EMBODIMENTS

Figure 1:
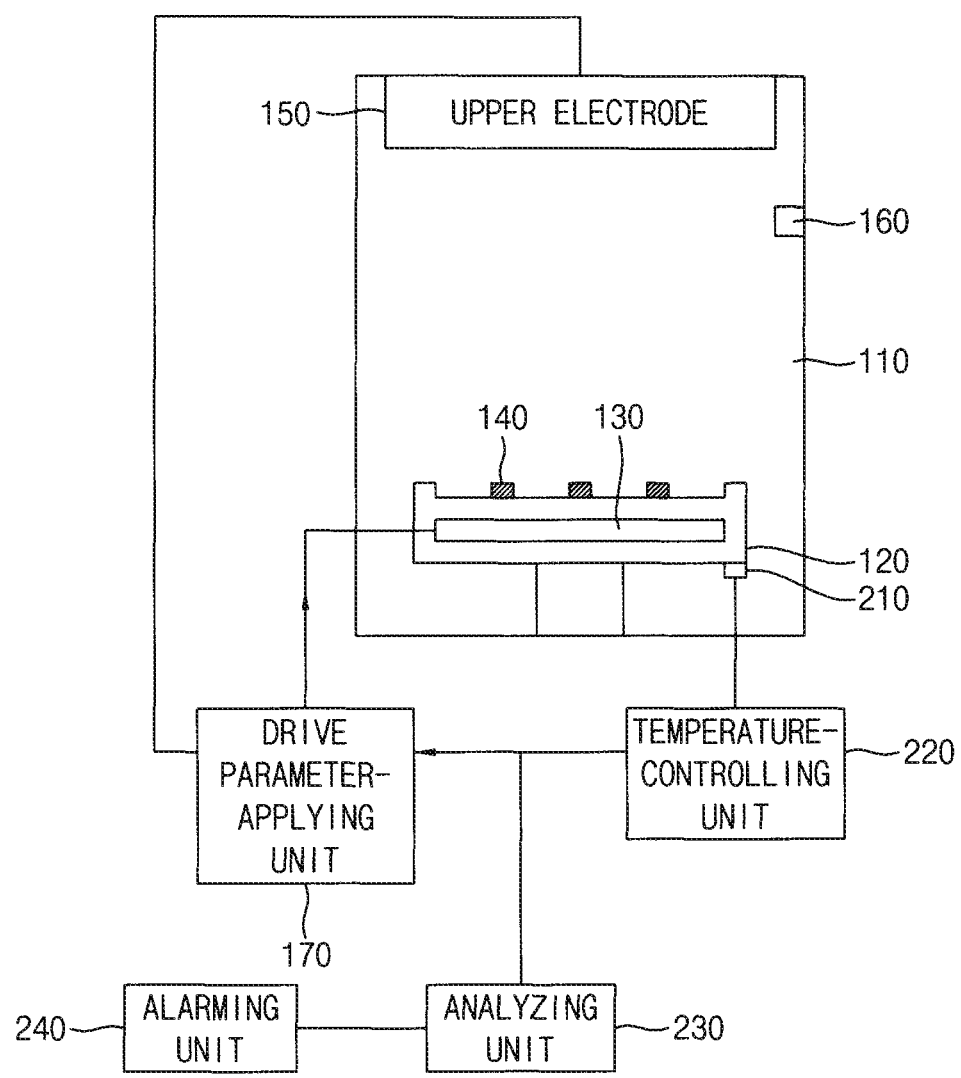
FIG. 1 is a functional block diagram of an apparatus for diagnosing an abnormal state of a substrate-processing apparatus in accordance with an embodiment of the present disclosure.

Reference will now be made in detail to the embodiments of the present general inventive concepts, examples of which are illustrated in the accompanying drawings, wherein like reference numerals refer to the like elements throughout. The embodiments are described below in order to explain the present general inventive concepts by referring to the figures.

Embodiments described herein relate to the diagnosis of an abnormal state of a substrate-processing apparatus. In some embodiments, the apparatus is a plasma-processing apparatus.

FIG. 1 is a functional block diagram of an apparatus for diagnosing an abnormal state of a substrate-processing apparatus in accordance with an embodiment of the present disclosure.

Referring to FIG. 1, in various embodiments, the substrate-processing apparatus includes a plasma-processing apparatus. The plasma-processing apparatus may include one ore more of a depositing apparatus, an etching apparatus, and an ashing apparatus. The depositing apparatus may be configured to form a layer on a semiconductor substrate using plasma. The etching apparatus may be configured to etch a layer on a semiconductor substrate using plasma. The ashing apparatus may be configured to remove a photoresist pattern on a semiconductor substrate using plasma.

The substrate-processing apparatus may include a chamber 110, a chuck 120, a heater 130, a lift pin 140, an upper electrode 150, a gas inlet 160 and a drive parameter-applying unit 170. The chuck 120 may be disposed on a bottom surface of the chamber 110. The chuck 120 may include an electrostatic chuck (ESC). The heater 130 may be installed in the chuck 120. The lift pin 140 may be capable of moving vertically within the chuck 120.

The upper electrode 150 may be disposed in an upper space of the chamber 110. The chuck 120 and the upper electrode 150 may be electrically connected with the drive parameter-applying unit 170. The drive parameter-applying unit 170 may be configured to apply drive parameters including one or more of a power, a current, a voltage, and a resistance to the chuck 120. The drive parameter-applying unit 170 may include a power transducer configured to transduce a power applied from a power source to the chuck 120. The gas inlet 160 may be connected to a sidewall of the chamber 110. Plasma may be generated from process gases, introduced into the chamber 110 at the gas inlet 160, by an electric field between the upper electrode 150 and the chuck 120.

Figure 2:
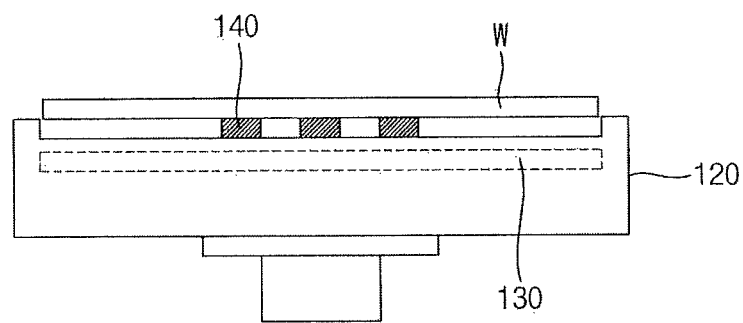
FIG. 2, FIG. 3 and FIG. 4 are cross-sectional views illustrating abnormal states in the substrate-processing apparatus.
Figure 3:
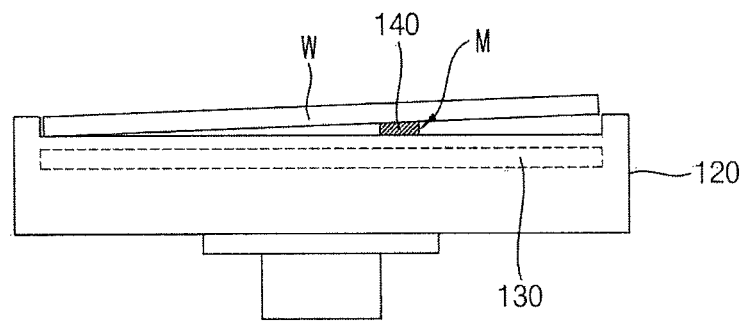
Figure 4:
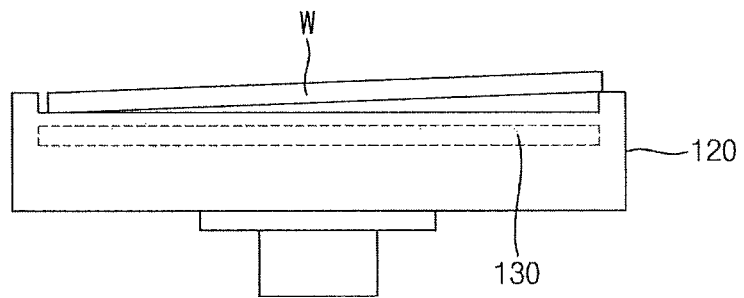

FIG. 2, FIG. 3, and FIG. 4 are cross-sectional views illustrating abnormal states in the substrate-processing apparatus. Referring to FIG. 2, a gap may be formed between a semiconductor substrate W and the chuck 120 due to malfunctions of the lift pin 140. Referring to FIG. 3, the semiconductor substrate W on the chuck 120 may be slightly inclined due to a foreign substance M on the chuck 120. Referring to FIG. 4, an edge portion of the semiconductor substrate W may be hung to an edge portion of the chuck 120 so that the semiconductor substrate W may be tilted. For example, the wafer W may be misaligned when positioned on the chuck 120, thereby causing the wafer W to overlap the chuck 120. Furthermore, the semiconductor substrate W may be bent or warped, resulting in a contact area between the bent semiconductor substrate W and the chuck 120 being reduced.

For the above-mentioned example cases, the contact area between the semiconductor substrate W and the chuck 120 may be decreased. Accordingly, heat from the heater 130 to the semiconductor substrate W may not be uniformly transferred, resulting in hot-spots on the wafer and excessive thermal gradients across the wafer. Thermal gradients may adversely affect the subsequent plasma processing steps.

Additionally, a chucking force of the chuck 120 for fixing the semiconductor substrate W may be weakened. The term "chucking force" refers to the force that the chuck 120 exerts against the wafer W (e.g. a vacuum force) to prevent the wafer W from moving during subsequent processing. In the presence of the example aforementioned faults, the chuck 120 may be exposed to the plasma for a long time, thereby eroding the chuck 120. Consequently, further deterioration may also be generated in the eroded chuck 120. A pressure in the chamber 110 may be beyond a set pressure range. Furthermore, a flow of a helium gas, which may function as to uniformly maintain a temperature in the chamber 110, may be radially changed. The aforementioned abnormal states should not be considered to limit the scope of this disclosure, as other abnormalities may exist in the placement of the wafer W on the chuck 120.

When the above-mentioned abnormal states may be generated in the substrate-processing apparatus, a temperature-compensating operation to the chuck 120 may be immediately performed by a temperature-controlling unit 220. Specifically, the temperature-compensating operation may be performed when the semiconductor substrate is being processed in the substrate-processing apparatus. Although at least one of the above-mentioned abnormal states may occur in the substrate-processing apparatus, the substrate-processing apparatus may continue to operate. A semiconductor device processed while the abnormal state is present, may be subsequently determined to be abnormal by a tester. Furthermore, the continuous operation of the abnormal substrate-processing apparatus may cause a serious breakdown of the substrate-processing apparatus.

An apparatus for diagnosing the abnormal state of the substrate-processing apparatus in accordance with example embodiments may be configured to diagnose generations of the above-mentioned abnormal states in the substrate-processing apparatus. Additionally, the diagnosing apparatus may be configured to detect a warpage of the semiconductor substrate W. The diagnosing apparatus may include a temperature sensor 210, a temperature-controlling unit 220, an analyzing unit 230 and an alarming unit 240.

The temperature sensor 210 may be attached to the chuck 120. The temperature sensor 210 may measure a temperature of the chuck 120. The temperature-controlling unit 220 may be configured to control the drive parameter-applying unit 170 in accordance with the temperature of the chuck 120 measured by the temperature sensor 210. The temperature-controlling unit 220 may transmit control signals to the drive parameter-applying unit 170 in accordance with the measured temperatures of the chuck 120. For example, when a measured temperature of the chuck 120 is lower than a target temperature of the chuck 120, the temperature-controlling unit 220 may input the control signal, which may increase (or adjust) one or more drive parameters provided from the drive parameter-applying unit 170 to the chuck 120. In contrast, when a measured temperature of the chuck 120 may be higher than the target temperature of the chuck 120, the temperature-controlling unit 220 may input the control signal, which may decrease (or adjust) the drive parameters provided from the drive parameter-applying unit 170 to the chuck 120.

The analyzing unit 230 may be configured to analyze the control signals transmitted from the temperature-controlling unit 220 to the drive parameter-applying unit 170. The analyzing unit 230 may compare the control signals with a predetermined reference control signal. Alternatively, the analyzing unit 230 may identify whether a waveform of the control signal may be matched with a waveform of the reference control signal or not. For example, the analyzing unit 230 may identify when the waveform of the control signal may be within an allowable range set from the waveform of the reference control signal. When the measured temperature of the chuck 120 may be within an allowable range set from the target temperature, the reference control signal may include a signal transmitted from the temperature-controlling unit 220 to the drive parameter-applying unit 170.

Therefore, when the control signal may not be within the allowable range from the reference control signal, or the waveform of the control signal may not be within the allowable range from the waveform of the reference control signal, the analyzing unit 230 may identify the presence or onset of the abnormal state in the substrate-processing apparatus. Furthermore, the analyzing unit 230 may identify the warpage of the semiconductor substrate W, even when abnormal states such as a lift pin malfunction, presence of a foreign substance or a misaligned wafer have not occurred.

In one embodiment, a control signal is a measured temperature of the chuck 120, and a waveform of the control signal is a time variant series of temperature measurements of the temperature of the chuck 120. In one non-limiting example, a waveform of the temperature of the chuck 120 oscillates where the chuck is rotatable, thereby indicating a location of the interface between the wafer W and the chuck 120 where the abnormality exists. In another non-limiting example, a ramping temperature waveform indicates the progression of the abnormality.

The alarming unit 240 may generate an alarm at the onset of the abnormal state in the substrate-processing apparatus as determined by the diagnosis of the analyzing unit 230. Furthermore, the alarming unit 240 may generate an alarm upon detecting the warpage of the semiconductor substrate W.

Additionally, the alarming unit 240 may provide an input to a system configured to provide overall control of the substrate-processing apparatus with the abnormal state of the substrate-processing apparatus or the warpage of the semiconductor substrate W, or both the abnormal state and the warped substrate W.

Figure 5:
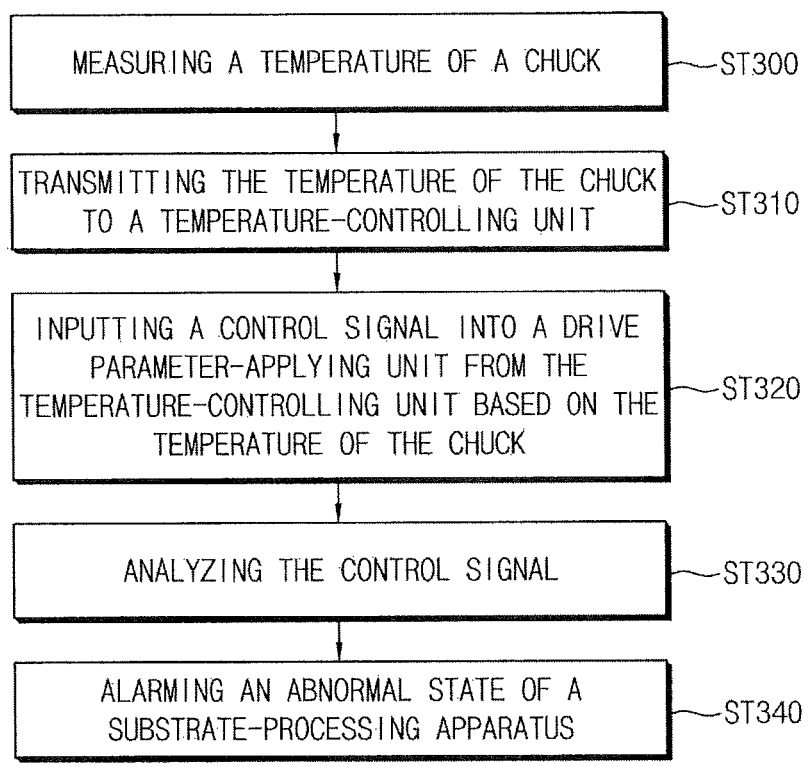
FIG. 5 is a flowchart representation of a method for diagnosing an abnormal state of a substrate-processing apparatus using the apparatus shown in FIG. 1.

FIG. 5 is a flow chart representation of a method for diagnosing an abnormal state of a substrate-processing apparatus using the apparatus in FIG. 1. Referring to FIG. 1 and FIG. 5, at step ST300, the temperature sensor 210 may measure the temperature of the chuck 120. At step ST310, the temperature of the chuck 120 measured by the temperature sensor 210 may be transmitted to the temperature-controlling unit 220. At step ST320, the temperature-controlling unit 220 may input the control signals into the drive parameter-applying unit 170 in accordance with the measured temperature of the chuck 120.

At step ST330, the analyzing unit 230 may analyze the control signals. The analyzing unit 230 may compare the control signals with the reference control signal. The analyzing unit 230 may identify when the waveform of the control signal may be within the allowable range set from the waveform of the reference control signal. When the measured temperature of the chuck 120 may be within the allowable range set from the target temperature, the analyzing unit 230 may determine the absence of the abnormal state in the substrate-processing apparatus. In this case, the control signal may be within the allowable range set from the reference control signal, or the waveform may be matched with the waveform of the reference control signal.

In contrast, when the measured temperature of the chuck 120 may not be within the allowable range from the target temperature, the analyzing unit 230 may determine that an abnormal state exists in the substrate-processing apparatus. In this case, the control signal may not be within the allowable range from the reference control signal, or the waveform of the control signal may not be within the allowable range from the waveform of the reference control signal.

At step ST340, the alarming unit 240 may generate an alarm upon detection of the abnormal state in the substrate-processing apparatus or upon detecting the warpage of the semiconductor substrate W by the diagnosis of the analyzing unit 230, or both. The alarming unit 240 may provide an input to a system for wholly controlling the substrate-processing apparatus when the abnormal state of the substrate-processing apparatus or the warpage of the semiconductor substrate W, or both, are detected.

Figure 6:
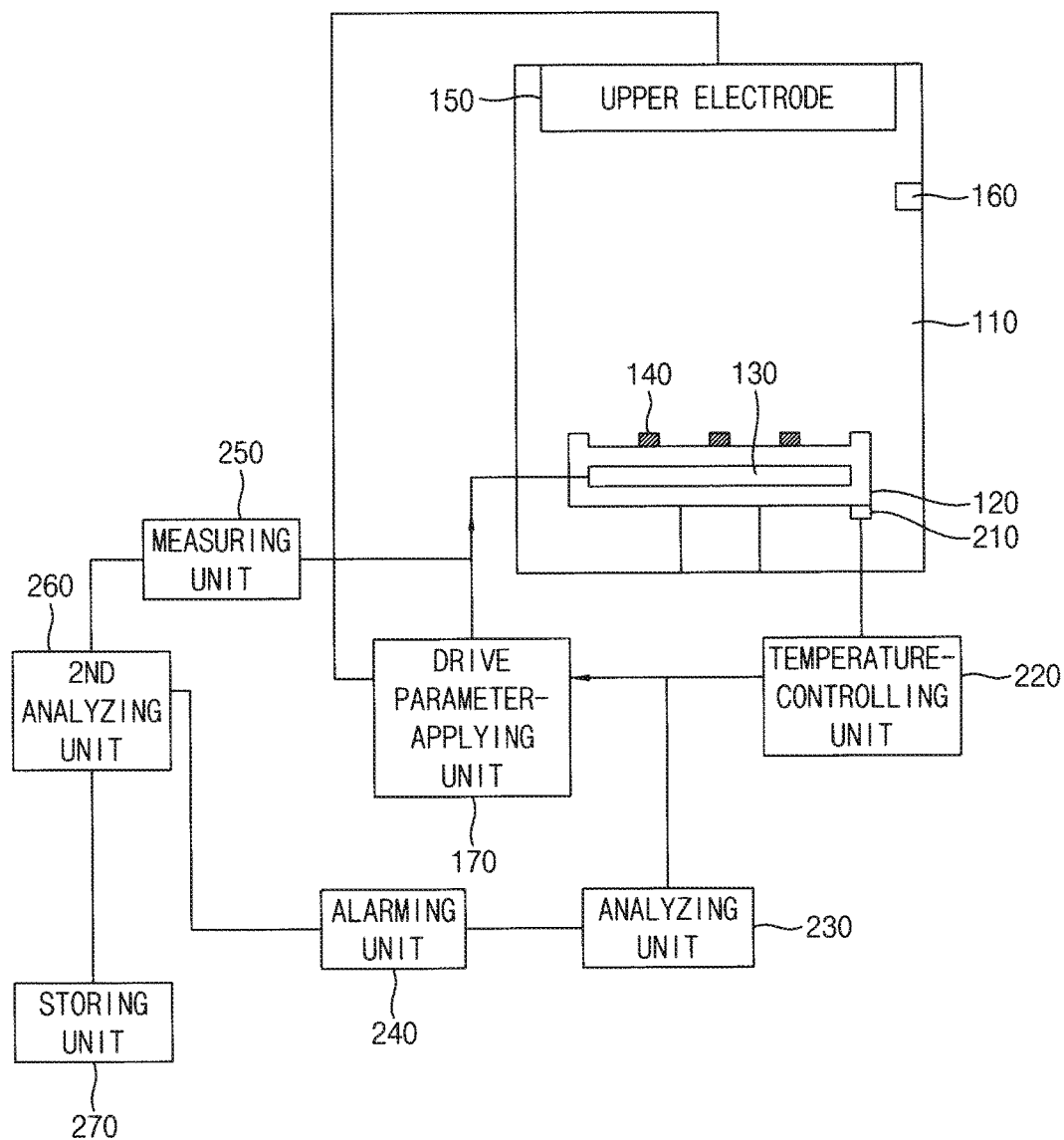
FIG. 6 is a functional block diagram of an apparatus for diagnosing an abnormal state of a substrate-processing apparatus in accordance with an embodiment of the present disclosure.

FIG. 6 is a functional block diagram of an apparatus for diagnosing an abnormal state of a substrate-processing apparatus in accordance with example embodiments. A diagnosing apparatus of this example embodiment may include elements substantially the same as those of the diagnosing apparatus in FIG. 1, except for the inclusion of a measuring unit, a second analyzing unit and a storing unit. The description of the elements in common between the embodiments shown in FIG. 1 and FIG. 6 will not be repeated, in the interest of brevity and clarity of description.

Referring to FIG. 6, the measuring unit 250 may be configured to measure the drive parameters applied from the drive parameter-applying unit 170 to the chuck 120. Because the drive parameters may include one or more of the power, the current, the voltage, and the resistance, the measuring unit 250 may include a various instrumentation including a voltmeter, and an ammeter.

The second analyzing unit 260 may be configured to analyze the drive parameters measured by the measuring unit 250. When the abnormal state may be generated in the substrate-processing apparatus, the control signal inputted from the temperature-controlling unit 220 to the drive parameter-applying unit 170 may not be within the allowable range set from the reference control signal. Furthermore, the waveform of the control signal may not be within the allowable range from the waveform of the reference control signal. Therefore, the drive parameters applied from the drive parameter-applying unit 170 to the chuck 120 may change significantly in response to the abnormality.

The second analyzing unit 260 may compare the measured drive parameters with a predetermined reference drive parameter. Alternatively, the second analyzing unit 260 may identify whether a waveform of the drive parameter may be within an allowable range set from a waveform of the reference drive parameter. When the measured temperature of the chuck 120 may be within an allowable range set from the target temperature, the reference drive parameter may include a parameter transmitted from the drive parameter-applying unit 170 to the chuck 120. Therefore, when the drive parameter is not within the allowable range from the reference drive parameter, or the waveform of the drive parameter is not within the allowable range from the waveform of the reference drive parameter, the second analyzing unit 260 may determine the presence of the abnormal state in the substrate-processing apparatus, the warpage of the semiconductor substrate W, or both.

According to this example embodiment, the abnormal state of the substrate-processing apparatus may be identified twice, first by the primary diagnosis of the first analyzing unit 230 based on the control signal transmitted from the temperature-controlling unit 220 to the drive parameter-applying unit 170, and second by the secondary diagnosis of the second analyzing unit 260 based on the drive parameters actually applied from the drive parameter-applying unit 170 to the chuck 120.

For example, although the abnormal state may occur in the substrate-processing apparatus, the first analyzing unit 230, (which may identify the abnormal state of the substrate-processing apparatus based on the control signal transmitted from the temperature-controlling unit 220 to the drive parameter-applying unit 170), may diagnose the non-generation of the abnormal state in the substrate-processing apparatus, the non-generation of the warpage in the semiconductor substrate W, or both. In this case, the second analyzing unit 260 may determine the presence of the abnormal state in the substrate-processing apparatus, the generation of the warpage in the semiconductor substrate W, or both, based on the drive parameter actually applied from the drive parameter-applying unit 170 to the chuck 120. Accordingly, either the analyzing unit 230, the second analyzing unit 260, or both, will detect the presence of an abnormality.

The analysis results of the second analyzing unit 260, (which may diagnose the abnormal state of the substrate-processing apparatus based on the drive parameter actually applied from the drive parameter-applying unit 170 to the chuck 120), may have a relatively higher reliability than that of the analysis results of the first analyzing unit 230, (which may diagnose the abnormal state of the substrate-processing apparatus based on the control signal transmitted from the temperature-controlling unit 220 to the drive parameter-applying unit 170).

The analysis results of the second analyzing unit 260 may be transmitted to the alarming unit 240. The alarming unit 240 may generate an alarm to indicate the presence of the abnormal state in the substrate-processing apparatus, the warpage of the semiconductor substrate W, or both, based on the diagnosis of the second analyzing unit 260. Additionally, the alarming unit 240 may provide an input to a system for controlling the substrate-processing apparatus based upon the abnormal state of the substrate-processing apparatus, the warpage of the semiconductor substrate W, or both. The drive parameters measured by the measuring unit 250 may be stored in the storing unit 270. A database of the drive parameters in the storing unit 270 may be used for an accurate diagnosis of the abnormal state in the substrate-processing apparatus. In various embodiments, the storing unit includes one or more of a non-volatile RAM, a volatile RAM and a ROM. In one example, the drive parameters are correlated to determine dependencies between power, current voltage and resistance changes by the drive parameter applying unit 170, thereby determining a type of abnormality. In another example, the drive parameters show a time variant pattern, which can indicate the type of abnormality present, the frequency of detected abnormalities, or an indication of wear in the components within the chamber—useful for maintenance of the chamber or for further diagnosis of detected abnormalities.

Figure 7:
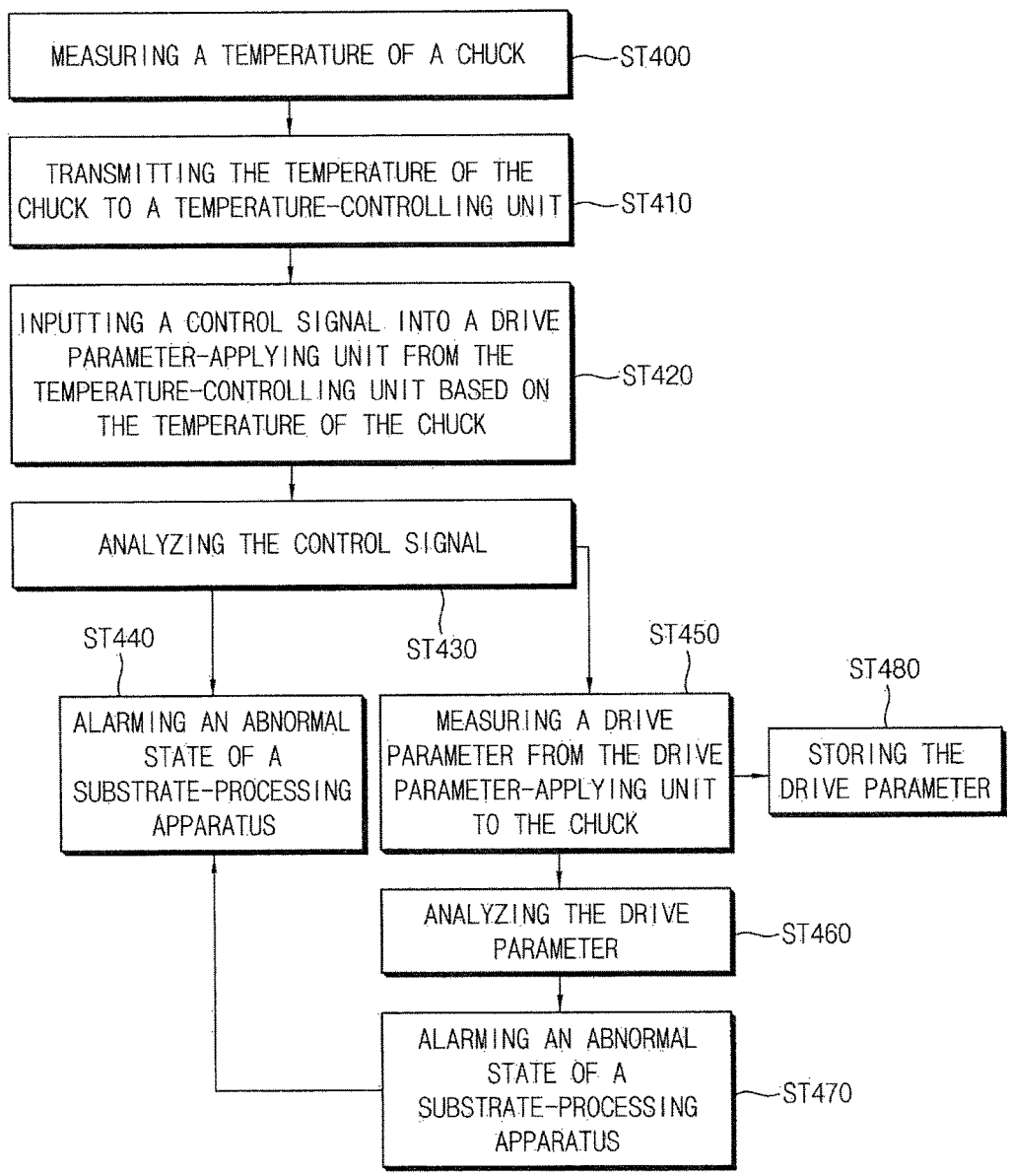
FIG. 7 is a flowchart representation of a method for diagnosing an abnormal state of a substrate-processing apparatus using the apparatus shown in FIG. 6.

FIG. 7 is a flow chart representation of a method for diagnosing an abnormal state of a substrate-processing apparatus using the apparatus in FIG. 6.

Referring to FIG. 6 and FIG. 7, at step ST400, the temperature sensor 210 may measure the temperature of the chuck 120. At step ST410, the temperature of the chuck 120, measured by the temperature sensor 210, may be transmitted to the temperature-controlling unit 220. At step ST420, the temperature-controlling unit 220 may input the control signals into the drive parameter-applying unit 170 in accordance with the measured temperature of the chuck 120.

At step ST430, the analyzing unit 230 may analyze the control signals. The analyzing unit 230 may compare the control signals with the reference control signal. The analyzing unit 230 may identify when the waveform of the control signal is within the allowable range set from the waveform of the reference control signal. When the measured temperature of the chuck 120 is within the allowable range set from the target temperature, the analyzing unit 230 may diagnose the non-generation of the abnormal state in the substrate-processing apparatus. In this case, the control signal may be within the allowable range set from the reference control signal, or may have the waveform matched with the waveform of the reference control signal.

In contrast, when the measured temperature of the chuck 120 is not within the allowable range from the target temperature, the analyzing unit 230 may identify the generation of the abnormal state in the substrate-processing apparatus. In this case, the control signal may not be within the allowable range from the reference control signal, or the waveform of the control signal may not be within the allowable range from the waveform of the reference control signal.

At step ST440, the alarming unit 240 may generate an alarm to indicate the presence of the abnormal state in the substrate-processing apparatus, the warpage of the semiconductor substrate W, or both, by the diagnosis of the analyzing unit 230. The alarming unit 240 may provide an input to a system for controlling the substrate-processing apparatus with the abnormal state of the substrate-processing apparatus, the warpage of the semiconductor substrate W, or both.

At step ST450, when the measured temperature of the chuck 120 may be within the target temperature, the measuring unit 250 may measure the drive parameters applied from the drive parameter-applying unit 170 to the chuck 120.

At step ST460, the second analyzing unit 260 may be configured to analyze the drive parameters measured by the measuring unit 250. The second analyzing unit 260 may compare the measured drive parameters with the reference drive parameter. Alternatively, the second analyzing unit 260 may identify whether a waveform of the drive parameter is within an allowable range set from a waveform of the reference drive parameter. When the drive parameter is within the allowable range from the reference drive parameter or the waveform of the drive parameter is within the allowable range from the waveform of the reference drive parameter, the second analyzing unit 260 may identify the non-generation (e.g. absence) of the abnormal state in the substrate-processing apparatus, the non-warpage of the semiconductor substrate W, or both.

In contrast, when the drive parameter is not within the allowable range from the reference drive parameter, or the waveform of the drive parameter is not within the allowable range from the waveform of the reference drive parameter, the second analyzing unit 260 may identify the generation of the abnormal state in the substrate-processing apparatus, the warpage of the semiconductor substrate W, or both.

At step ST470, the alarming unit 240 may generate an alarm to indicate the presence of the abnormal state in the substrate-processing apparatus, the warpage of the semiconductor substrate W, or both, by the diagnosis of the second analyzing unit 260. The alarming unit 240 may provide an input to a system for wholly controlling the substrate-processing apparatus with the abnormal state of the substrate-processing apparatus, the warpage of the semiconductor substrate W, or both.

At step ST480, the drive parameters measured by the measuring unit 250 may be stored in the storing unit 270. A database of the drive parameters in the storing unit 270 may be used for an accurate diagnosis of the abnormal state in the substrate-processing apparatus.

Figure 8:
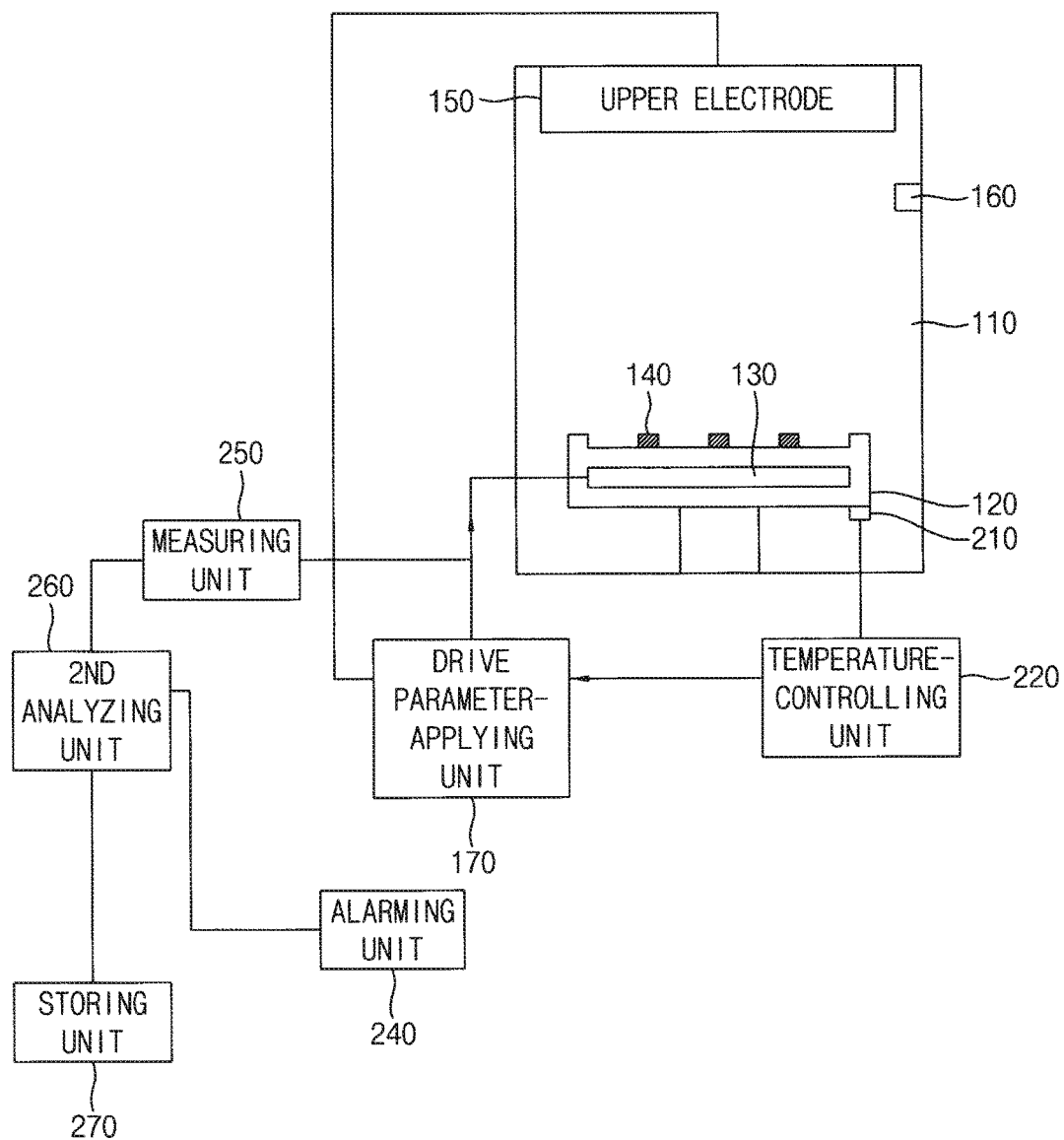
FIG. 8 is a functional block diagram of an apparatus for diagnosing an abnormal state of a substrate-processing apparatus in accordance with an embodiment of the present disclosure.

FIG. 8 is a functional block diagram of an apparatus for diagnosing an abnormal state of a substrate-processing apparatus in accordance with an embodiment of the present disclosure. Referring to, FIG. 8, a diagnosing apparatus may include a temperature sensor 210, a temperature-controlling unit 220, a measuring unit 250, an analyzing unit 260, an alarming unit 240 and a storing unit 270. The temperature sensor 210, the temperature-controlling unit 220 and the alarming unit 240 in FIG. 8 may have functions substantially the same as those of the temperature sensor 210, the temperature-controlling unit 220 and the alarming unit 240 in FIG. 1. The second measuring unit 250, the analyzing unit 260 and the storing unit 270 in FIG. 8 may have functions substantially the same as those of the second measuring unit 250, the second analyzing unit 260 and the storing unit 270 in FIG. 6.

Figure 9:
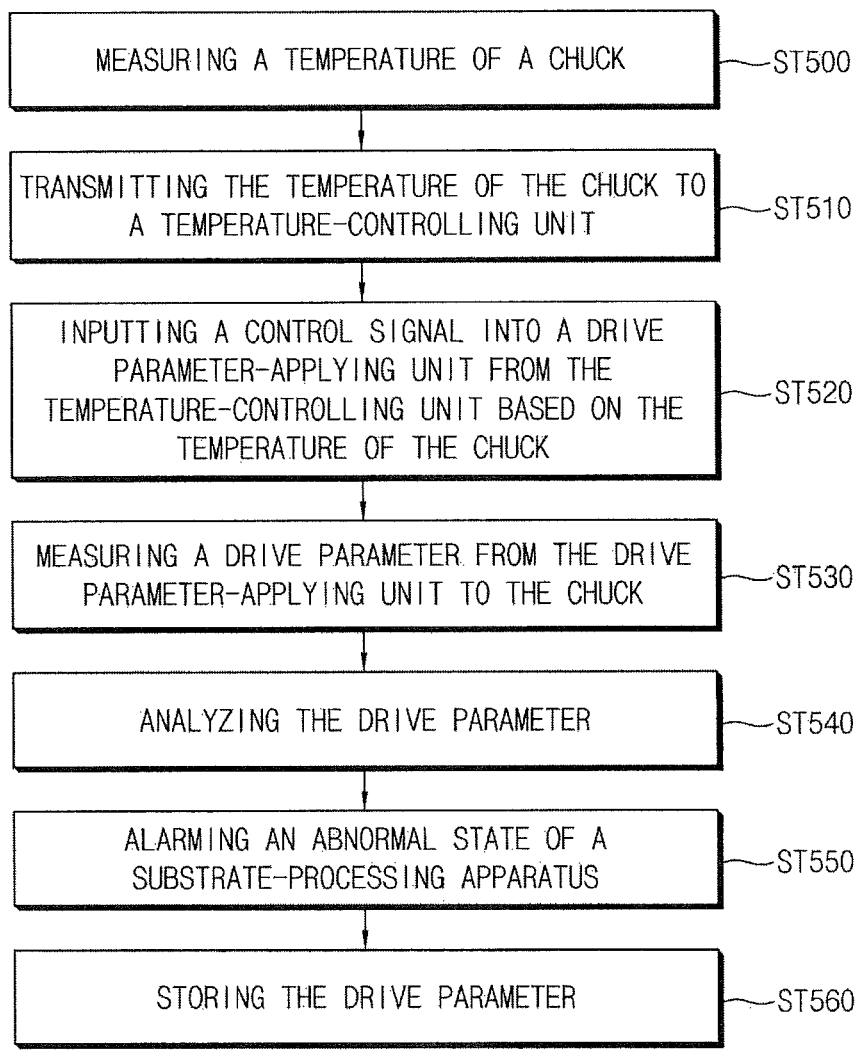
FIG. 9 is a flowchart representation of a method for diagnosing an abnormal state of a substrate-processing apparatus using the apparatus in FIG. 8.

FIG. 9 is a flow chart representation of a method for diagnosing an abnormal state of a substrate-processing apparatus using the apparatus in FIG. 8. Referring to FIG. 8 and FIG. 9, at step ST500, the temperature sensor 210 may measure the temperature of the chuck 120. At step ST510, the temperature of the chuck 120 measured by the temperature sensor 210 may be transmitted to the temperature-controlling unit 220. At step ST520, the temperature-controlling unit 220 may input the control signals into the drive parameter-applying unit 170 in accordance with the measured temperature of the chuck 120. At step ST530, the measuring unit 250 may measure the drive parameters applied from the drive parameter-applying unit 170 to the chuck 120.

At step ST540, the analyzing unit 260 may analyze the drive parameters measured by the measuring unit 250. The analyzing unit 260 may compare the measured drive parameters with the reference drive parameter. Alternatively, the analyzing unit 260 may identify whether a waveform of the drive parameter may be within an allowable range set from a waveform of the reference drive parameter. When the drive parameter is within the allowable range from the reference drive parameter, or the waveform of the drive parameter is within the allowable range from the waveform of the reference drive parameter, the analyzing unit 260 may identify the absence of the abnormal state in the substrate-processing apparatus, the non-warpage of the semiconductor substrate W, or both.

In contrast, when the drive parameter is not within the allowable range from the reference drive parameter, or the waveform of the drive parameter is not within the allowable range from the waveform of the reference drive parameter, the analyzing unit 260 may identify the presence of the abnormal state in the substrate-processing apparatus, the warpage of the semiconductor substrate W, or both.

At step ST550, the alarming unit 240 may provide an alarm indicating the presence of the abnormal state in the substrate-processing apparatus, the warpage of the semiconductor substrate W, or both, by the diagnosis of the analyzing unit 260. The alarming unit 240 may provide an input to a system for controlling the substrate-processing apparatus with the abnormal state of the substrate-processing apparatus, the warpage of the semiconductor substrate W, or both.

At step ST560, the drive parameters measured by the measuring unit 250 may be stored in the storing unit 270. A database of the drive parameters in the storing unit 270 may be used for an accurate diagnosis of the abnormal state in the substrate-processing apparatus.

The methods and the apparatuses of the example embodiments may accurately diagnose a tiny abnormal state (e.g. a minor fault, or a fault having minimal impact on the temperature applied to the chuck 120) of the substrate-processing apparatus, which may not be identified by the temperature-compensating operation of the temperature-controlling unit 220. Particularly, the abnormal state of the substrate-processing apparatus may be identified in-situ, while the wafer is being processed by the substrate-processing apparatus. Accordingly, the processing of the semiconductor device may be interrupted to correct the abnormality, and improve the yield of the semiconductor device. Furthermore, the abnormal state of the substrate-processing apparatus may be immediately diagnosed to increase a life span of the substrate-processing apparatus.

The methods and the apparatuses of example embodiments may be applied to the control paths of the chuck 120 using the measured temperature of the chuck 120. Alternatively, the methods and the apparatuses of example embodiments may be applied to control paths of other elements in the substrate-processing apparatus controlled by sensors.

According to example embodiments, the control signals transmitted from the temperature-controlling unit to the drive parameter-applying unit may be analyzed to accurately diagnose one or more of the abnormal state of the substrate-processing apparatus and the warpage of the semiconductor substrate. Thus, the abnormal state of the substrate-processing apparatus may be recognized rapidly and accurately to improve a yield of a semiconductor device. Furthermore, the abnormal substrate-processing apparatus may be rapidly repaired.

Although a few embodiments of the present general inventive concepts have been shown and described, it will be appreciated by those skilled in the art that changes may be made in these embodiments without departing from the principles and spirit of the general inventive concepts, the scope of which is defined in the appended claims and their equivalents.

What is claimed is:

1. A method of diagnosing an abnormal state of a substrate-processing apparatus comprising:
   measuring a temperature of a chuck in the substrate-processing apparatus;
   comparing the measured temperature of the chuck to a target temperature of the chuck, with a temperature-controlling unit; and
   analyzing a control signal to diagnose an abnormal state of the substrate-processing apparatus, the control signal transmitted from the temperature-controlling unit to a drive parameter-applying unit configured to provide the chuck with a drive parameter,
   wherein the abnormal state indicates at least one of an inaccurate placement of a substrate on the chuck and a warped substrate on the chuck.

2. The method of claim 1, wherein diagnosing the abnormal state of the substrate-processing apparatus comprises at least one of identifying whether the control signal is within an allowable range set from a reference control signal, and whether a waveform of the control signal is within an allowable range set from a waveform of the reference control signal.

3. The method of claim 1, further comprising generating an alarm to indicate the abnormal state of the substrate-processing apparatus.

4. The method of claim 1, further comprising:
   measuring the drive parameter applied from the drive parameter-applying unit to the chuck; and
   analyzing the measured drive parameter to diagnose the abnormal state of the substrate-processing apparatus.

5. The method of claim 4, wherein diagnosing the abnormal state of the substrate-processing apparatus comprises identifying at least one of whether the measured drive parameter is within an allowable range set from a reference drive parameter and whether a waveform of the measured drive parameter is within an allowable range set from a waveform of the reference drive parameter.

6. The method of claim 4, further comprising generating an alarm to indicate the abnormal state of the substrate-processing apparatus.

7. The method of claim 4, further comprising storing the measured drive parameter.

8. The method of claim 4, wherein the drive parameter comprises at least one of a power, a voltage and a current.

* * * * *